US007820679B2

(12) United States Patent
Tonge et al.

(10) Patent No.: US 7,820,679 B2
(45) Date of Patent: Oct. 26, 2010

(54) N-(-3-METHOXY-5-METHYLPYRAZIN-2-YL)-2-(4-'1,3,4-OXADIAZOL-2-YL-PHENYL) PYRIDINE-3 SULPHONAMIDE AS AN ANTICANCER AGENT

(75) Inventors: David William Tonge, Macclesfield (GB); Sian Tomiko Taylor, Macclesfield (GB); Francis Thomas Boyle, Macclesfield (GB); Andrew Mark Hughes, Macclesfield (GB); Donna Johnstone, Macclesfield (GB); Marianne Bernice Ashford, Macclesfield (GB); Nigel Charles Barrass, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 1590 days.

(21) Appl. No.: 10/524,963

(22) PCT Filed: Aug. 20, 2003

(86) PCT No.: PCT/GB03/03653

§ 371 (c)(1),
(2), (4) Date: Feb. 18, 2005

(87) PCT Pub. No.: WO2004/018044

PCT Pub. Date: Mar. 4, 2004

(65) Prior Publication Data

US 2006/0094729 A1 May 4, 2006

(30) Foreign Application Priority Data

Aug. 23, 2002 (GB) .................................. 0219660.8

(51) Int. Cl.
*A01N 43/54* (2006.01)
*A01N 43/40* (2006.01)
*A01N 43/82* (2006.01)
*C07D 239/42* (2006.01)
*C07D 401/04* (2006.01)
*A61K 31/445* (2006.01)
*A61K 31/41* (2006.01)

(52) U.S. Cl. ........................ 514/256; 514/315; 514/364
(58) Field of Classification Search ........................ None
See application file for complete search history.

(56) References Cited

U.S. PATENT DOCUMENTS

| 5,464,853 | A | 11/1995 | Chan et al. |
| 5,514,691 | A | 5/1996 | Chan et al. |
| 5,843,902 | A | 12/1998 | Garnick et al. |
| 5,866,568 | A * | 2/1999 | Bradbury et al. ......... 514/227.8 |
| 2002/0055457 | A1 | 5/2002 | Janus |
| 2003/0092757 | A1 | 5/2003 | Singh et al. |
| 2005/0014769 | A1 | 1/2005 | Osswald et al. |

FOREIGN PATENT DOCUMENTS

| EP | 510526 A1 | 10/1992 |
| EP | 526708 A1 | 2/1993 |
| EP | 558258 A1 | 9/1993 |
| EP | 569193 A1 | 11/1993 |
| EP | 640596 A1 | 3/1995 |
| EP | 682016 A1 | 11/1995 |
| EP | 749964 A1 | 12/1996 |
| EP | 1 256 344 A1 | 11/2002 |
| EP | 1 424 080 A1 | 6/2004 |
| GB | 2295616 | 6/1996 |
| WO | WO 94/27979 A1 | 12/1994 |
| WO | WO 95/26957 A1 | 10/1995 |
| WO | WO 96/09818 A1 | 4/1996 |
| WO | WO 96/40681 | 12/1996 |
| WO | WO 98/40332 | 9/1998 |
| WO | WO 99/48530 A1 | 9/1999 |
| WO | WO 99/56761 A1 | 11/1999 |
| WO | WO 00/21509 A2 | 4/2000 |
| WO | WO 00/36918 A1 | 6/2000 |
| WO | WO 00/67024 A1 | 11/2000 |
| WO | WO 01/00198 A2 | 1/2001 |
| WO | WO 01/44239 | 6/2001 |
| WO | WO 01/60370 | 8/2001 |
| WO | WO 01/91736 A2 | 12/2001 |
| WO | WO 02/11713 A2 | 2/2002 |
| WO | WO 02/49630 | 6/2002 |
| WO | WO 02/069906 A2 | 9/2002 |
| WO | WO 02/074034 A2 | 9/2002 |
| WO | WO 02/080960 A2 | 10/2002 |
| WO | WO 02/085351 A1 | 10/2002 |
| WO | WO 03/006041 A1 | 1/2003 |
| WO | WO 03/009805 A2 | 2/2003 |
| WO | WO 03/015820 A1 | 2/2003 |
| WO | WO 03/039539 A2 | 5/2003 |

(Continued)

OTHER PUBLICATIONS

Hsu et al. "ET-1 Expression and Growth Inhibition of Prostate Cancer Cells: A Retinoid Target with Novel Specificity". Cancer Research. 1998; 58:4817-4822.*

(Continued)

*Primary Examiner*—Leslie A. Royds

(57) ABSTRACT

The use of N-(3-methoxy-5-methylpyrazin-2-yl)-2-(4-[1,3,4-oxadiazol-2-yl]phenyl)pyridine-3-sulphonamide, or a pharmaceutically acceptable salt thereof, in the treatment of cancer and/or pain in a warm blooded animal such as man is described.

9 Claims, 1 Drawing Sheet

FOREIGN PATENT DOCUMENTS

Figure 1:
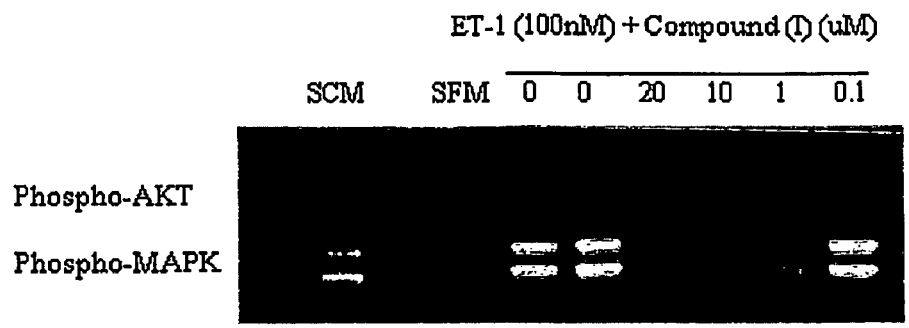

| WO | WO 03/045434 A2 | 6/2003 |
|---|---|---|
| WO | WO 2004/032922 A1 | 4/2004 |
| WO | WO 2004/035057 | 4/2004 |
| WO | WO 2005/023264 | 3/2005 |
| WO | 2005/063735 A1 | 7/2005 |
| WO | WO 2005/080403 | 9/2005 |
| WO | 2006/056760 A1 | 6/2006 |
| WO | 2007/010235 A1 | 1/2007 |

OTHER PUBLICATIONS

Bradbury, Robert, H et al, "New Non-peptide Endothelin-A Receptor Antagonists: Synthesis, Biological Properties, and Structure-Activity Relationships of 5-(Dimethylamino)-N-pyridyl-, -N-pyrimidinyl, -N-pyridazinyl-, and -N-pyrazinyl-1-naphthalenesulfonamides", J Med Chem, May 14, 1997, 996-1004, 40.

Brooks N. et al, "ZD4054—a specific endothelin-A receptor antagonist providing hope for treatment of HRPC", 4th PacRim Breast and Prostate Cancer Meeting. British Columbia, Canada, Aug. 12-16, 2008. abstract.

Carducci M.A. et al, "Targeting bone metastasis in prostate cancer with endothelin receptor antagonists", Clin Cancer Res, 2006, 6296s-6300s, 12.

Carducci, M.A. et al, "The Endothelin-A Receptor Antagonist Atrasentan (ABT-627) Delays Clinical Progression in Hormone Refractory Prostate Cancer: a Multinational, Randomized, Double-Blind, Placebo-Controlled Trial", Asco Abstracts 2001.

Carragher N. et al "Application of 3-dimensional (3D) in vitro invasion assays demonstrate anti-invasive activity of the specific endothelin-A (ETA) receptor-antagonist ZD4054 when combined with the novel Src/Abl inhibitor AZD0530"NCRI. Birmingham, UK, Oct. 5-8, 2008; abst B77.

Chiao, J.W. et al, "Endothelin-1 from Prostate Cancer Cells is enhanced by bone contact which blocks osteoclastic bone resorption", British Journal of Cancer, 2000, 360-365, 83(3).

Chirgwin, J.M. et al, "Tumor-bone cellular interactions in skeletal metastases", J Musculoskel Neuron Interact, 2004, 308-318, 4(3).

Clarkson-Jones J. et al, "Metabolism of [14C]-ZD4054 in healthy volunteers", Drug Metab Rev, 2008, 206, 40 (Suppl 3) (Abstract 283).

Clarkson-Jones J. et al, "Metabolism of [14C]-ZD4054 in healthy volunteers", poster, ISSX—15th North American Regional Meeting, San Diego, USA, Oct. 12-16, 2008.

Curwen J et al, "The impact of ZD4054, a specific endothelin-A receptor antagonist, on tumor blood supply, invasion and the bone microenvironment" Mol Cancer Ther, 2007;6(12) Suppl II:abst A272.

Curwen J et al, "The impact of ZD4054, a specific endothelin-A receptor antagonist, on tumor blood supply, invasion and the bone microenvironment", AACR-NCI-EORTC, San Francisco, USA, Oct. 22-26, 2007. Poster.

Curwen, J. et al, "The specific endothelin A receptor antagonist ZD4054 reduces tumour-induced angiogenesis in a preclinical model", 10th International Conference on Endothelin (ET-10). Bergamo, Italy, Sep. 16-19, 2007; oral presentation.

Curwen, J. et al, "The specific endothelin A receptor antagonist ZD4054 reduces tumour-induced angiogenesis in a preclinical model", 10th International Conference on Endothelin (ET-10). Bergamo, Italy, Sep. 16-19, 2007; poster.

Dawson N. et al, "Impact of the specific endothelin-A (ETA) receptor antagonist ZD4054 on overall survival and bone metastasis in patients with hormone-resistant prostate cancer: results of a Phase II trial", Current Treat Options Oncol 2008; 105-107, 9(Suppl 1).

Dawson N. et al, "Impact of the specific endothelin-A (ETA) receptor antagonist ZD4054 on overall survival and bone metastasis in patients with hormone-resistant prostate cancer: results of a Phase II trial", oral presentation, Chemotherapy Foundation Symposium, New York, USA, Nov. 4-7, 2008.

Dawson N. et al,"Impact of the specific endothelin A receptor antagonist ZD4054 on overall survival and bone metastasis in patients with hormone-resistant prostate cancer: results of a Phase II trial", ASCO GU Congress, San Francisco, USA Feb. 14-16, 2008, Genitourinary Cancers Symposium Proceedings 2008;abst 7.

Dawson N. et al,"Impact of the specific endothelin A receptor antagonist ZD4054 on overall survival and bone metastasis in patients with hormone-resistant prostate cancer: results of a Phase II trial", ASCO GU Congress, San Francisco, USA Feb. 14-16, 2008, poster.

Dingemanse, J. et al, "Pharmacokinetics and pharmacodynamics of tezosentan, an intravenous dual endothelin receptor antagonist, following chronic infusion in healthy subjects", Br J Clin Pharmacol, Apr. 28, 2002, 355-362, 53.

Fizazi K.et al, "The Effects of Endothelin-1 and Abt-627, and Endothelin-1 Antagonist, in an in Vitro Model of Bone Metastases from Prostate Cancer", Asco Abstracts 2001.

Godara G. et al, "Distinct Patterns of Endothelin Axis Expression in Primary Prostate Cancer", Urology, 2007, 209-215, vol. 70(1).

Godara G. et al, "Role of Endothelin Axis in progression to Aggressive Phenotype of Prostate Adenocarcinoma", The Prostate, 2005, 27-34, 65.

Gross-Goupil M. et al, "Integrating Molecular Oncology into Therapeutic Strategies for Prostate Cancer", European Urology Supplements, 2009, 114-119, 8.

Growcott J. et al "ZD4054—A small-molecule, specific endothelin-A receptor antagonist: providing hope for patients with hormone-resistant prostate cancer", AZ-Manchester Cancer Research Centre Showcase. Manchester, UK, Sep. 22, 2008.

Growcott J. et al, "Anti-invasive activity of the specific endothelin-A receptor (ETAR) antagonist, ZD4054, in A673 rhabdomyosarcoma cells", 10th International Conference on Endothelin (ET-10). Bergamo, Italy, Sep. 16-19, 2007. Poster.

Growcott J. et al, "Anti-invasive activity of the specific endothelin-A receptor (ETAR) antagonist, ZD4054, in A673 rhabdomyosarcoma cells", 10th International Conference on Endothelin (ET-10). Bergamo, Italy, Sep. 16-19, 2007. Oral Presentation.

Growcott J.W. et al, "Phenotypic in vitro differentiation of the specific endothelin A receptor antagonist, ZD4054, from the selective endothelin antagonist, atrasentan", Mol Cancer Ther, 2007; 6(12) Suppl II:abst B269.

Growcott J.W. et al, "Phenotypic in vitro differentiation of the specific endothelin A receptor antagonist, ZD4054, from the selective endothelin antagonist, atrasentan", AACR-NCI-EORTC, San Francisco, USA, Oct. 22-26, 2007. Poster.

Growcott, J.W., "Preclinical anticancer activity of the specific endothelin A receptor antagonist ZD4054", Anti-Cancer Drugs 2009, 00:000-000.

Guise T. et al, "Endothelin A Receptor Blackade Inhibits Osteoblastic Metastases", Asco Abstracts 2001.

Hickinson D.M. et al, "Enhanced in vitro anti-invasive activity in A673 rhabdomyosarcoma cells of the specific endothelin-A receptor (ETA) antagonist ZD4054 when combined with the novel Src inhibitor AZD0530", Proc Am Assoc Cancer Res, 2008,49 :abst 1487.

Hickinson D.M. et al, "Enhanced in vitro anti-invasive activity in A673 rhabdomyosarcoma cells of the specific endothelin-A receptor (ETA) antagonist ZD4054 when combined with the novel Src inhibitor AZD0530", AACR Annual Meeting, San Diego, CA, USA, Apr. 12-16, 2008. Poster.

Isherwood B. et al "Enhanced in vitro anti-invasive activity in A673 rhabdomyosarcoma cells of the specific endothelin-A (ETA) antagonist ZD4054 when combined with the novel Src/Abl inhibitor AZD0530" NCRI. Birmingham, UK, Oct. 5-8, 2008; poster.

James N, et al, "The potent, specific endothelin A receptor antagonist ZD4054 improves overall survival in patients with pain-free or mildly symptomatic M1 hormone-resistant prostate cancer" 1st European Multidisciplinary Meeting on Urological Cancers. Barcelona, Spain, Nov. 2-4, 2007;abst O2.

James N. "New clinical data for the specific ETA receptor antagonist ZD4054", EAU 2008 Milan Italy, Mar. 26-29, 2008. Oral presentation.

James N. et al, "The effect of ZD4054 on bone metastases in patients with M1 hormone-resistant prostate cancer as assessed by radionuclide bone scans", 1st European Multidisciplinary Meeting on Urological Cancers. Barcelona, Spain, Nov. 2-4, 2007;abst P10.

James N. et al, "The effect of ZD4054 on bone metastases in patients with M1 hormone-resistant prostate cancer as assessed by radionuclide bone scans", 1st European Multidisciplinary Meeting on Urological Cancers. Barcelona, Spain, Nov. 2-4, 2007. Poster.

James N.D. et al, "ZD4054, a potent, specific endothelin A receptor antagonist, improves overall survival in pain-free or mildly symptomatic patients with hormone-resistant prostate cancer (HRPC) and bone metastases" ECCO 14, Barcelona, Spain, Sep. 23-27, 2007. Oral Presentation.

James, N.D. et al, "Safety and Efficacy of the Specific Endothelin-A Receptor Antagonist ZD4054 in Patients with Hormone-Resistant Prostate Cancer and Bone Metastases Who Were Pain Free or Mildly Symptomatic: A Double-Blind, Placebo-Controlled, Randomised, Phase 2 Trial" Eur Urol (2008), doi:10.1016/j.eururo.2008.11.002.

James, N.D. et al, "ZD4054, a potent, specific endothelin A receptor antagonist, improves overall survival in pain-free or mildly symptomatic patients with hormone-resistant prostate cancer (HRPC) and bone metastases", European Journal of Cancer Supplements, 2007, abstract 3LB, vol. 5, No. 6.

Kenyon A. et al, "The mystery of the co-eluting peak"; DMDG meeting. Cambridge, UK, Sep. 17-19, 2007. Poster.

Knight L.J. et al, "Hypermethylation of endothelin receptor type B (EDNRB) is a frequent event in non-small cell lung cancer", Proc Am Assoc Cancer Res, 2007, 48:abst 1135.

Knight L.J. et al, "Hypermethylation of endothelin receptor type B (EDNRB) is a frequent event in non-small cell lung cancer", AACR, Los Angeles, CA, USA, Apr. 14-18, 2007. Poster.

Knight, L.J., "Epigenetic silencing of the endothelin-B receptor gene in non-small cell lung cancer", International Journal of Oncology, 2009, 465-471, 34.

Kopetz, Scott E et al, "Endothelin-1 as a target for therapeutic intervention in prostate cancer", Investigational New Drugs, May 2002, 173-182, 20.

Mohammad K., et al, "Combined endothelin A receptor antagonist and bisphosphonate treatment more effectively reduces prostate cancer growth in bone than either alone", American Society for Bone and Mineral Research, 27th Annual Meeting. 2005; 1213a.

Nelson J.B.et al, "Endothelin-1 inhibits apoptosis in prostate cancer", Neoplasia 2005, 631-7, 7(7) (abstract).

Nelson J.B.et al, "The Endothelin Axis: Emerging Role in Cancer", Nature Reviews Cancer, 2003, 110-116, 3.

Nelson J.B.et al, "The Endothelin-A Receptor Antagonist Atrasentan (ABT-627) Reduces Skeletal Remodeling Activity in Men with Advance Refractory Prostate Cancer", Asco Abstracts 2001.

Payne H. et al, "Progression-free survival, overall survival and bone metastasis in a phase II trial of the specific endothelin a receptor antagonist ZD4054 in patients with hormone-resistant prostate cancer", CURy congress. Barcelona, Spain, Jan. 31-Feb. 3, 2008. oral presentation.

Pflug BR et al, "Defining the basis of an operational model for enhanced efficacy of combination therapy using an endothelin receptor antagonist and chemotherapeutic agents", Mol Cancer Ther, 2007;6(12) Suppl II:abst A287.

Ranson M, et al, "The pharmacokinetic and tolerability profile of once-daily oral ZD4054 in Japanese and Caucasian patients with hormone-refractory prostate cancer", Eur J Cancer Suppl 2007, 112-113, 5(4) (Abstract 718).

Ranson M, et al, "The pharmacokinetic and tolerability profile of once-daily oral ZD4054 in Japanese and Caucasian patients with hormone-refractory prostate cancer", ECCO 14, Barcelona, Spain, Sep. 23-27, 2007. Poster.

Rosano L, et al, "Endothelin A receptor/beta-arrestin signaling is critical for ovarian cancer metastasis: novel molecular therapeutic applications", Eur J Cancer Supp 2008; 54, 6 (Abstract 168).

Rosano L. et al, "Endothelin A receptor promotes ovarian cancer metastasis: implications for an effective targeted-therapy", Proc Am Assoc Cancer Res, 2008, 49:abst 2574.

Rosano L. et al, "Endothelin A receptor promotes ovarian cancer metastasis: implications for an effective targeted-therapy", AACR Annual Meeting, San Diego, CA, USA, Apr. 12-16, 2008. Presentation.

Rosano L. Et al, "β-Arrestin 1 as messenger of endothelin A receptor to mediate β-catenin signaling and epithelial to mesenchymal transition in human ovarian cancer cells", Proc Am Assoc Cancer Res, 2007, 48:abst 5636.

Rosano L.A. et al, "Endothelin-1 promotes proteolytic activity of ovarian carcinoma", Clinical Science, Aug. 2002, 306S-309S, 103 (Supplement 48).

Rosano, L. et al, "Emerging role of β-arrestin in endothelin A receptor-mediated signaling in the metastatic progression of ovarian cancer: implications for an effective targeted therapy", AACR: Advances in cancer research: from the laboratory to the clinic. Jordan, Mar. 16-19, 2008;abst PR15.

Rosano, L. et al, "Emerging role of β-arrestin in endothelin A receptor-mediated signaling in the metastatic progression of ovarian cancer: implications for an effective targeted therapy", AACR: Advances in cancer research: from the laboratory to the clinic. Jordan, Mar. 16-19, 2008;oral presentation.

Rosano, L. et al, "ZD4054, a Potent Endothelin Receptor A Antagonist, Inhibits Ovarian Carcinoma Cell Proliferation", Experimental Biology and Medicine, 2006, 1132-1135, 231.

Smollich M. et al, "Specific endothelin A receptor antagonist ZD4054 reduces breast cancer cell migration and invasion and exhibits synergistic effects with aromatase inhibitors and fulvestrant", AACR: Advances in cancer research: from the laboratory to the clinic. Jordan, Mar. 16-19, 2008; abst PR8.

Smollich M. et al, "Specific endothelin A receptor antagonist ZD4054 reduces breast cancer cell migration and invasion and exhibits synergistic effects with aromatase inhibitors and fulvestrant", AACR: Advances in cancer research: from the laboratory to the clinic. Jordan, Mar. 16-19, 2008; presentation.

Smollich, M. et al, "Targeting the endothelin system: novel therapeutic options in gynaecological, urological and breast cancers", Expert Rev. Anticancer Ther., 2008, 1481-1493, 8(9).

Stensland B. et al, "N-(3-methoxy-5-methylpyrazin-2-yl)-2[4-(1,3,4-oxadiazol-2- yl)phenyl]pyridine-3-sulfonamide (ZD4054 Form 1)", Acta Crystallogr Section E Structure Rep, 2004; o1817-o1819, 60(10).

Swaisland H. et al, "Clinical drug interactions with ZD4054 in healthy, male volunteers", 1st European Multidisciplinary Meeting on Urological Cancers. Barcelona, Spain, Nov. 2-4, 2007;abst P84.

Swaisland H. et al, "Clinical drug interactions with ZD4054 in healthy, male volunteers", 1st European Multidisciplinary Meeting on Urological Cancers. Barcelona, Spain, Nov. 2-4, 2007; poster.

Venuti et al, "An Endothelin a Receptor Antagonist as New Antitumor Agent in HPV Associated Cervical Carcinoma", Asco Abstracts 2001.

Verhar et al; "Pharmacokinetics and pharmacodynamic effects of ABT-627, an oral ETA selective endothelin antagonist, in humans", Brit. J. Clin. Pharmacology, 2000, 562-573, 49.

Warren R. et al, "ZD4054: a specific endothelin A receptor antagonist with promising activity in metastatic castration-resistant prostate cancer", Expert Opin. Investig. Drugs, 2008, 1237-1245, 17(8).

Williams E.D., "The combination of a specific endothelin A receptor antagonist ZD4054 and submaximal bisphosphonate pamidronate prevents bone metastasis", EORTC-NCI-AACR, Prague, Czech Republic, Nov. 7-10, 2006. Poster.

Williams ED et al, "The combination of the specific endothelin A receptor antagonist ZD4054 and submaximal bisphosphonate pamidronate prevents soft-tissue metastasis", Mol Cancer Ther, 2007;6(12) Suppl II:abst A271.

Williams, E.D. et al, "The combination of a specific endothelin A receptor antagonist ZD4054 and submaximal bisphosphonate pamidronate prevents bone metastis," European Journal of Cancer Supplements, 2006, 15, vol. 4, No. 12.

Wulfing P. et al, "ZD4054, a specific endothelin A receptor antagonist, reduces breast cancer cell migration and invasion and exhibits additive effects with aromatase inhibitors and fulvestrant", Mol Cancer Ther, 2007;6(12) Suppl II: abst A275.

Wulfing P. et al, "ZD4054, a specific endothelin A receptor antagonist, reduces breast cancer cell migration and invasion and exhibits additive effects with aromatase inhibitors and fulvestrant", AACR-NCI-EORTC, San Francisco, USA, Oct. 22-26, 2007. Poster.

Zonnenberg B. et al, "The effect of ZD4054 on bone metastasis in patients with M1 hormone-resistant prostate cancer", Calcif Tissue Int, 2008; 82 (Suppl 1):S95 (Abstract P093).

Zonnenberg B. et al, "The effect of ZD4054 on bone metastasis in patients with M1 hormone-resistant prostate cancer", ECTS (35th European Symposium on Calcified Tissues), Barcelona, Spain, May 24-28, 2008. Poster.

Pflug, et al., Defining the basis of an operational model for enhanced efficacy of combination therapy using an endothelin receptor antagonist and chemotherapeutic agents; EORTC Meeting Oct. 2007.

Rosano, L. et al., Combined Targeting of Endothelin A Receptor and the Epidermal Growth Factor Receptor in Ovarian Cancer Shows Enhanced Antitumor Activity, Cancer Research, Jul. 1, 2007, vol. 67(13).

Rosano, L. et al., ZD4054, a specific antagonist of the endothelin A receptor, inhibits tumor growth and enhances cytotoxicity of paclitaxel in human ovarian carcinoma in vitro and in vivo. Proceedings of the American Association of Cancer Research Apr. 16-20, 2005; 46, Abs 5830.

Rosano, L. et al., ZD4054, a specific antagonist of the endothelin A receptor, inhibits tumor growth and enhances paclitaxel activity in human ovarian carcinoma in vitro and in vivo, Mol Cancer Ther., 2007, Nov. 2003. Jul;6(7).

Williams, E.D., The Combination of Specific Endothelin A Receptor Antagonist ZD4054 and Submaximal Bisphosphonate Pamidronate Prevents Soft-Tissue Metastasis, AAC-NCI-EORTC Molecular Targets and Cancer Therapeutics Conference, Oct. 22-Oct. 26, 2007, San Francisco, CA USA.

Laura Rosano et al; ZD4054, a specific antagonist of the endothelin A receptor, inhibits tumor growth and enhances cytotoxicity of paclitaxel in human ovarian carcinoma in vitro and in vivo; AACR, Anaheim/Orange County, CA, Apr. 16-20, 2005.

Curtis N. et al; ZD4054 specifically inhibits endothelin A receptor-mediated anti-apoptotic effects, but not endothelin B receptor-mediated pro-apoptotic effects; AACR-NCI-EORTC, Geneva, Switzerland, Sep. 28-Oct. 1, 2004.

Glenn Liu et al; Tolerability profile of ZD4054 is consistent with the effects of endothelin A receptor-specific antagonism; ASCO Annual Meeting, Orlando, Florida, May 13-17, 2005.

Morris C et al; ZD4054: specificity for endothelin A receptor following single-dose administration in healthy volunteers; AACR-NCI-EORTC, Geneva, Switzerland, Sep. 28-Oct. 1, 2004.

Dreicer R et al; ZD4054 specifically inhibits endothelin A receptor-mediated effects but not endothelin B receptor-mediated effects; ASCO Prostate Cancer Symposium, Orlando, Florida, Feb. 17-19, 2005.

Martin Todd et al; Metabolite Factories: Use of microbial systems to generate metabolites of an endothelin receptor antagonist; Biotrans 2005, Delft, The Netherlands, Jul. 3-Jul. 8, 2005.

Morris et al; Specific inhibition of the endothelin A receptor with ZD4054: clinical and preclinical evidence; British Journal of Cancer (2005) 92, 2148-2152.

Morris Michael J et al : Clinical approaches to osseous metastases in prostate cancer. The Oncologist, 2003, 161-173, vol. 8, No. 2.

Curtis N. et al; ZD4054 Specifically Inhibits Endothelin A Receptor-Mediated Anti-Apoptotic Effects, But Not Endothelin B receptor-mediated pro-apoptotic effects; AACR-NCI-EORTC, Geneva, Switzerland, Sep. 28-Oct. 1, 2004.

Curtis et al; ZD4054 blocks ET-1-stimulated phosphorylation of p44/42 mitogen-activated protein kinase and proliferation of osteoblast cells; AACR, Anaheim/Orange County, CA, Apr. 16-20, 2005.

Morris et al; ZD4054 reduces endothelin-1-induced forearm vasoconstriction in healthy male volunteers; AACR, Anaheim/Orange County, CA, Apr. 16-20, 2005.

Laura Rosano et al; Combined targeting of the endothelin receptor and the epidermal growth factor receptor in ovarian cancer shows enhanced antiproliferative effects; AACR 2006, Apr. 1-5, 2006, Washington, DC.

J O Curwen et al; ZD4054 : a specific endothelin A receptor antagonist with potential utility in prostate cancer and metastatic bone disease European Journal of Cancer, Pergamon Press, Oxford, GB, vol. 38, Nov. 2002, p. S102, XP004403782.

Carducci M A et al : "Endothelin Receptor Antagonist, ABT-627, for Prostate Cancer : Initial Trial Results" Journal of Urology, Baltimore, MD, US, vol. 161, No. 4, Suppl, Apr. 1999, p. 176.

Nelson J B et al : "The Role of Endothelin-1 and Endothelin Receptor Antagonists in Prostate Cancer" BJU International, Blackwell Science, Oxford, GB, vol. 85, No. Suppl 2, Apr. 2000, pp. 45-48.

Jarvis M F et al : "ABT-627, an Endothelin ETA Receptor-Selective Antagonist, Attenuates Tactile Allodynia in a Diabetic Rat Model of Neuropathic Pain" European Journal of Pharmacology, Amsterdam, NL, vol. 388, No. 1, Jan. 24, 2000, pp. 29-35.

Database WPI Section Ch, Week 200163 Derwent Publications Ltd ., London, GB; AN 2001-565331, (2001).

Nelson JB "Endothelin-1 Production and Decreased endothelin B Receptor Expression in advanced Prostate Cancer" Cancer Research 56, 663-668, Feb. 15, 1996.

Kroodsma JM/ Rabelink AJ "Endothelinen: mogelijk een nieuw farmacologisch aangrijpingspunt bij hart-en vaatziekten, nierziekten en oncologische aandoeningen" Nederlands Tijdschrift Voor Geneeskunde, Sep. 20, 1997, 141, 38, 1806-10 +English Abstract.

An abstract reporting the symposium "Endothelin Inhibitors: Exploring Novel Therapeutics" Meeting Report (Jun. 25, 1999) Washington DC, USA, Jun. 7-8, 1999.

Boven E An abstract by reporting from the "American Society of Clinical Oncology—$35^{th}$ Annual Meeting (Part I)" Meeting Report (Sep. 13, 2001), Atlanta, GA, USA, May 15-18, 1999.

McKinnon C An abstract by reporting from the "American Society of Clinical Oncology—$35^{th}$ Annual Meeting (Part IV)" Meeting Report (Sep. 13, 2001), Atlanta, GA, USA, May 15-18, 1999.

Adeniyi A An abstract by reporting from the "American Urological Association—$94^{th}$ Annual Meeting" Meeting Report (Aug. 26, 1999), Dallas, TX, USA, May 1-6, 1999.

Boven E "American Society of Clinical Oncology—$35^{th}$ Annual Meeting" IDrugs, (1999) 2/7 (617-619), Atlanta, GA, USA, May 15-18, 1999.

McKinnon C "Topoisomerase Inhibitors and Other New Agents", IDrugs, (1999) 2/7 (629-632) Atlanta, GA, USA, May 15-18, 1999.

Adeniyi A "American Urological Association—$94^{th}$ Annual Meeting" IDrugs, (1999) 2/7 (656-658), Dallas, TX, USA, May 1-6, 1999.

Nelson JB "Editorial: Endothelin Receptor Antagonists in the Treatment of Prostate Cancer" The Prostate 49: 91-92 (2001) Pittsburgh, PA USA.

Nelson JB; Carducci MA "The Role of the Endothelin Axis in Prostate Cancer" The Prostate Journal. vol. 1, No. 3, May / Jun. 1999, 126-130.

Nelson JA; Hedican SP "Identification of Endothelin-1 in the Pathophysiology of Metastic Adenocarcinoma of the Prostate" Nature Medicine, vol. 1, No. 9, Sep. 1995, 944-949.

Curwen JO; Wilson C "ZD4054: A Specific Endothelin a Receptor Antagonist with Potential Utility in Prostate Cancer and Metastic Bone Disease" EORTC-NCI-AACR, Frankfurt, Germany AstraZeneca Poster presented Nov. 19-22, 2002.

Bagnato A; Raffaele Tecce "Autocrine Actions of Endothelin-1 as a Growth Factor in Human Ovarian Carcinoma Cells" Clinical Cancer Research, 1995, vol. 1, 1059-1066.

Wu-Wong JR "Endothelin Attenuates Apoptosis in Human Smooth Muscle Cells" Biochemical Journal, 1997, vol. 328, No. 3, 733-737, Abbott Park, IL USA.

Spinella, F "Endothelin-1 Induces Vascular Endothelial Growth Factor by Increasing Hypoxia-Inducible Factor-1a in Ovarian Carcinoma Cells*" J Biological Chemistry, 2002, 277 (31), 27850-27855, Rome Italy.

Rosano, Laura et al: "Therapeutic targeting of the endohelin a receptor in human ovarian carcinoma"; Cancer Research, vol. 63, No. 10, May 15, 2003, pp. 2447-2453, XP002365689.

Walczak, Jr et al: "Pharmacological Treatments for Prostate Cancer; Expert Opinion on Investigantional Drugs", Ashley Publications Ltd., London, GB, vol. 11, No. 12, 2002, pp. 1737-1748, XP009008862.

James et. al. Safety and Efficacy of the Specific Endothelin-A Receptor Antagonist ZD4054 in Patients with Hormone-Resistant Prostate Cancer and Bone Metastases Who Were Pain Free or Mildly Symptomatic: A Double-Blind, Placebo-Controlled, Randomised, Phase 2 Trial; European Urology 55 (2009) 1112-1123.

Fizazi et. al. Specific Endothelin-A Receptor Antagonism for the Treatment of Advanced Prostate Cancer; Institut Gustave Roussy, University of Paris XI, Villejuif, France, and *Charité, Universitätsmedizin Berlin, Berlin, Germany; 2009 The Authors; Journal Compliation; 2009 BJU International; 1-3.

New endothelin•A receptor antagonist prolongs survival; Research Highlights; Nature Reviews, Urology; vol. 6, Jul. 2009; p. 350.

Bialecki et al., A Novel Orally Active Endothelin-A Receptor Antagonist, ZD1611, Prevents Chronic Hypoxia-Induced Pulmonary Hypertension in the Rat, 1998, 114, 91S, American College of Chest Physicians, US.

Bialecki, R.A. IBC's Conference on Pulmonary Hypertension: New Understanding for Therapeutic Development. Expert Opinion on Investigational Drugs,1998, 653-658, 7(4).

Bialecki et al. ZD1611, an orally active endothelin-A receptor antagonist, prevents chronic hypoxia-induced pulmonary hypertension in the rat. Pulm Pharmacol Ther, 1999, 303-312, 12(5).

Bialecki et al. Zeneca ZD1611, an orally active endothelin-A receptor antagonist, prevents chronic hypoxia-induced pulomonary hypertension in the rat. Am J Respir Crit Care Med, 1997, A790, 155(4, Part 2).

Douglas S., Clinical development of endothelin receptor antagonists, Trends in Pharmacological Sciences, 1997, 408-412, 18.

Gang Liu, Chapter 8. Recent Advances in Endothelin Antagonism, 2000, 73-82, Annual Reports in Medicinal Chemistry.

Jeffery T. et al., Pulmonary vascular remodeling: a target for therapeutic intervention in pulmonary hypertension, Pharmacology & Therapeutics, 2001, 1-20, 92, Australia.

Rumsey el al. Development and progression of pulmonary hypertension is decreased by a novel orally active endothelin-A antagonist, ZD1611. 1997, Annu Congr Eur Respir Soc (ERS) (Sep. 20-24, Berlin), Abst 2782.

Wilson et al. Pharmacological profile of ZD1611, a novel, orally active endothelin ETA receptor antagonist. J Pharmacol Exp Ther, 1999, 1085-1091, 290(3).

Wilson et al. Zeneca ZD1611: A novel endothelin ETA receptor antagonist. 1997, Pharmacology 97 (Mar. 7-11, San Diego), Abst 312.

* cited by examiner

N-(-3-METHOXY-5-METHYLPYRAZIN-2-YL)-2-(4-'1,3,4-OXADIAZOL-2-YL-PHENYL)PYRIDINE-3 SULPHONAMIDE AS AN ANTICANCER AGENT

CROSS-REFERENCE TO RELATED APPLICATIONS

This application is a U.S. National Stage under 35 U.S.C §371 of International Application No. PCT/GB2003/003653 (filed Aug. 20, 2003) which claims priority under 35 U.S.C. §119(a)-(d) to Application No. GB0219660.8 filed on Aug. 23, 2002.

The present application refers to N-(3-methoxy-5-methylpyrazin-2-yl)-2-(4-[1,3,4-oxadiazol-2-yl]phenyl)pyridine-3-sulphonamide, or a pharmaceutically acceptable salt thereof, hereafter "Compound (I)", and its use in the treatment of cancer in a warm blooded animal such as man. The invention also relates to the use of pharmaceutical compositions containing Compound (I), or a pharmaceutically acceptable salt thereof, in a method of treating cancer in a warm blooded animal such as man, and to the use of Compound (I), or a pharmaceutically acceptable salt thereof, in the manufacture of medicament for use in a method of treating cancer in a warm blooded animal such as man. The invention also relates to the use of pharmaceutical compositions containing Compound (I), or a pharmaceutically acceptable salt thereof, in a method of treating pain in a warm blooded animal such as man, and to the use of Compound (I), or a pharmaceutically acceptable salt thereof, in the manufacture of medicament for use treating pain in a warm blooded animal such as man.

Cancer affects an estimated 10 million people worldwide. This figure includes incidence, prevalence and mortality. More than 4.4 million cancer cases are reported from Asia, including 2.5 million cases from Eastern Asia, which has the highest rate of incidence in the world. By comparison, Europe has 2.8 million cases, North America 1.4 million cases, and Africa 627,000 cases.

In the UK and US, for example, more than one in three people will develop cancer at some point in their life. Cancer mortality in the U.S. is estimated to account for about 600,000 a year, about one in every four deaths, second only to heart disease in percent of all deaths, and second to accidents as a cause of death of children 1-14 years of age. The estimated cancer incidence in the U.S. is now about 1,380,000 new cases annually, exclusive of about 900,000 cases of non-melanotic (basal and squamous cell) skin cancer.

Cancer is also a major cause of morbidity in the UK with nearly 260,000 new cases (excluding non-melanoma skin cancer) registered in 1997. Cancer is a disease that affects mainly older people, with 65% of cases occurring in those over 65. Since the average life expectancy in the UK has almost doubled since the mid nineteenth century, the population at risk of cancer has grown. Death rates from other causes of death, such as heart disease, have fallen in recent years while deaths from cancer have remained relatively stable. The result is that 1 in 3 people will be diagnosed with cancer during their lifetime and 1 in 4 people will die from cancer. In people under the age of 75, deaths from cancer outnumber deaths from diseases of the circulatory system, including ischaemic heart disease and stroke. In 2000, there were 151,200 deaths from cancer. Over one fifth (22 per cent) of these were from lung cancer, and a quarter (26 per cent) from cancers of the large bowel, breast and prostate.

Worldwide, the incidence and mortality rates of certain types of cancer (of stomach, breast, prostate, skin, and so on) have wide geographical differences which are attributed to racial, cultural, and especially environmental influences. There are over 200 different types of cancer but the four major types, lung, breast, prostate and colorectal, account for over half of all cases diagnosed in the UK and US. Prostate cancer is the fourth most common malignancy among men worldwide, with an estimated 400,000 new cases diagnosed annually, accounting 10 for 3.9 percent of all new cancer cases.

Current options for treating cancers include surgical resection, external beam radiation therapy and/or systemic chemotherapy. These are partially successful in some forms of cancer, but are not successful in others. There is a clear need for new therapeutic treatments.

Non-steroidal anti-inflammatory drugs SAIDS) and opiates are the main classes of drugs in pain relief. However both possess undesirable side effects. NSAIDS are known to cause gastrointestinal irritation and opiates are known to be addictive. There is thus also a clear need for new treatments for the management and treatment of pain.

Recently, endothelin A receptor antagonists have been identified as potentially of value in the treatment of cancer (Cancer Research, 56, 663-668, Feb. $15^{th}$, 1996 and Nature Medicine, Volume 1, Number 9, September 1999, 944-949).

The endothelins are a family of endogenous 21 amino acid peptides comprising three isoforms, endothelin-1 (ET-1), endothelin-2 and endothelin-3. The endothelins are formed by cleavage of the $Trp^{21}$-$Val^{22}$ bond of their corresponding proendothelins by an endothelin converting enzyme. The endothelins are among the most potent vasoconstrictors known and have a characteristic long duration of action. They exhibit a wide range of other activities including cell proliferation and mitogenesis, extravasation and chemotaxis, and also interact with a number of other vasoactive agents.

The endothelins are released from a range of tissue and cell sources including vascular endothelium, vascular smooth muscle, kidney, liver, uterus, airways, intestine and leukocytes. Release can be stimulated by hypoxia, shear stress, physical injury and a wide range of hormones and cytokines. Elevated endothelin levels have been found in a number of disease states in man including cancers.

The present invention concerns the surprising finding that Compound (I) is a particularly potent anti-cancer agent. Compound (I) is described as an endothelin receptor antagonist in WO96/4068 1, and although in WO96/40681 it is acknowledged that elevated endothelin levels have been found in a number of disease states in man including certain cancers, there is no hint or suggestion that this compound would possess the particular beneficial efficacious, metabolic and toxicological profiles that makes it such a potent anti-cancer agent. WO96/4068 1 claims the endothelin receptors described therein solely for cardiovascular diseases. For example in the introduction it is stated these compounds are useful in the treatment of diseases or medical conditions including "hypertension, pulmonary hypertension, cardiac or cerebral circulatory disease and renal disease". The claims list the following medical disease states "hypertension, pulmonary hypertension, congestive heart failure, dyslipidaemia, atherosclerosis, restenosis, acute and chronic renal failure, ischaemic stroke, subarachnoid haemorrhage, intermittent claudication, critical limb ischaemia, asthma or organ failure after general surgery or transplantation". There is no hint or suggestion from WO96/40681 that this compound would possess the particular beneficial efficacious, metabolic and toxicological profiles that makes it such a potent anti-cancer agent. In fact, the present inventors have surprisingly established that Compound (I) is a specific endothelin-A ($ET_A$) antagonist and has no measurable activity against endothelin-B ($ET_B$).

The ET$_A$ receptor has been shown, via a variety of mechanisms, to be the more important pathological receptor of the two identified endothelin receptors in oncology: in the reduction of abnormal cell proliferation (Bagnato et. al., (1995), Clin Cancer Res 1, 1059-1066); as a anti-apoptotic (Wu Wang et. al., (1997), Biochem J,. 328, 733-737); as an anti-angiogenic agent (Spinella et al., (2002), J. Biol. Chem, 227(31), 27850-27855); and as an inhibitor of bone metastases (Guise et. al., ASCO (2000) abstract 331 and Nelson, et. al., (1999), Urology 53, 1063-1069) in addition to mediating pain which is a common co-morbidity in cancer. It has been shown (Dahlof et al., (1990), J Hypertens, 8, 811-817) that large doses of endothelin-1 causes pain, and causes pain sensitization, but that this can be inhibited by an ETA antagonist (e.g. Davar et al., (1998), Neuroreport 9, 2279-2283 and De Mello et al., (1998), Pain, 77, 261-269). Therefore in another aspect of the invention, Compound (I) is administered for the prevention or treatment of pain mediated by the endothelin system, in particular that associated with elevated endothelin-1 levels.

Conversely, there is emerging evidence (e.g. Cattaruzza et. al., (2002), FASEB J. 14(7), 991-998 and Okazawa et. al., (1998), J Biol Chem, 273, 12581-12592) that the ET$_B$ receptor is involved in apoptotic signalling. The blocking of pro-apoptotic pathways would be undesirable in the treatment of cancer, hence a compound that specifically targeted the ET$_A$ receptor while leaving the ET$_B$ receptor unaffected would be of the greatest utility in the treatment of cancer. Compound (I) is such a compound.

Compound (I) by acting specifically on the ET$_A$ receptor has many advantages over endothelin antagonists that also have measurable ET$_B$ activity. For instance Compound (I) could be administered to a patient without the administrator or prescribing medical practitioner needing to titrate the dose of Compound (I) looking for signs of ET$_B$ activity (for example oedema). Furthermore, larger doses could potentially be administered because there would be no ET$_B$ side effects.

Another disadvantage of ET$_B$ inhibition is that it causes a rise in plasma endothelin. Potentially, over the course of treatment, for a mixed ET$_A$/ET$_B$ inhibitor, or a compound that selectively targeted the ET$_A$ receptor, but still had measurable ET$_B$ activity, this would result in increasingly larger doses of inhibitor being needed to have the same beneficial ET$_A$ effects. A specific ET$_A$ inhibitor would not encounter this problem.

Therefore according to the present invention, there is provided Compound (I), or a pharmaceutically acceptable salt thereof, for use in the treatment of cancer in a warm blooded animal such as man.

In one aspect, where Compound (I), or a pharmaceutically acceptable salt thereof, is referred to this refers to the compound only. In another aspect this refers to a pharmaceutically acceptable salt of Compound (I).

According to another feature of the present invention, there is provided Compound (I), or a pharmaceutically acceptable salt thereof, in the manufacture of a medicament for use in the treatment of cancer in a warm blooded animal such as man.

According to a further feature of this aspect of the invention there is provided a method of treating cancer which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use in the treatment of cancer in a warm blooded animal such as man.

In another aspect of the invention there is provided the use of Compound (I), or a pharmaceutically acceptable salt thereof, in the reduction of abnormal proliferation in a cancerous cell or inducing differentiation of a cancerous cell in a warm blooded animal such as man.

In another aspect of the invention there is provided the use of Compound (I), or a pharmaceutically acceptable salt thereof, in the manufacture of a medicament for use in the reduction of abnormal proliferation in a cancerous cell or inducing differentiation of a cancerous cell in a warm blooded animal such as man.

In another aspect of the invention there is provided a method for reducing abnormal proliferation in a cancerous cell or inducing differentiation of a cancerous cell which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use in the reduction of abnormal proliferation in a cancerous cell or inducing differentiation of a cancerous cell in a warm blooded animal such as man.

In another aspect of the invention there is provided the use of Compound (I), or a pharmaceutically acceptable salt thereof, in inducing apoptosis in a cancerous cell in a warm blooded animal such as man.

In another aspect of the invention there is provided the use of Compound (I), or a pharmaceutically acceptable salt thereof, in the manufacture of a medicament for use in inducing apoptosis in a cancerous cell in a warm blooded animal such as man.

In another aspect of the invention there is provided a method of inducing apoptosis in a cancerous cell which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use in inducing apoptosis in a cancerous cell in a warm blooded animal such as man.

In another aspect of the invention there is provided the use of Compound (I), or a pharmaceutically acceptable salt thereof, as an anti-angiogenic and vascular targeting agent in blood vessels supplying a cancerous cell in a warm blooded animal such as man.

In another aspect of the invention there is provided the use of Compound (I), or a pharmaceutically acceptable salt thereof, in the manufacture of a medicament for use as an anti-angiogenic and vascular targeting agent in blood vessels supplying a cancerous cell in a warm blooded animal such as man.

In another aspect of the invention there is provided a method of providing an anti-angiogenic and vascular targeting agent in blood vessels supplying a cancerous cell which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use as an anti-angiogenic and vascular targeting agent in blood vessels supplying a cancerous cell in a warm blooded animal such as man.

By the term "vascular targeting agent" it is to be understood that the site of action of Compound (I) would be on the vasculature itself rather than the tumour.

In another aspect of the invention there is provided the use of Compound (I), or a pharmaceutically acceptable salt thereof, as an anti-angiogenic agent in a warm blooded animal such as man.

In another aspect of the invention there is provided the use of Compound (I), or a pharmaceutically acceptable salt thereof, in the manufacture of a medicament for use as an anti-angiogenic agent in a warm blooded animal such as man.

In another aspect of the invention there is provided a method of providing an anti-angiogenic effect which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use as an anti-angiogenic agent in a warm blooded animal such as man.

In another aspect of the invention there is provided the use of Compound (I), or a pharmaceutically acceptable salt thereof, as an inhibitor of bone metastases and an inhibitor of invasion in a warm blooded animal such as man.

In another aspect of the invention there is provided the use of Compound (I), or a pharmaceutically acceptable salt thereof, in the manufacture of a medicament for use as an inhibitor of bone metastases and an inhibitor of invasion in a warm blooded animal such as man.

In another aspect of the invention there is provided a method of inhibiting bone metastases and inhibiting invasion which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use as an inhibitor of bone metastases and an inhibitor of invasion in a warm blooded animal such as man.

In another aspect of the invention there is provided the use of Compound (I), or a pharmaceutically acceptable salt thereof, as an inhibitor of bone metastases in a warm blooded animal such as man.

In another aspect of the invention there is provided the use of Compound (I), or a pharmaceutically acceptable salt thereof, in the manufacture of a medicament for use as an inhibitor of bone metastases in a warm blooded animal such as man.

In another aspect of the invention there is provided a method of inhibiting bone metastases which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use as an inhibitor of bone metastases in a warm blooded animal such as man.

In another aspect of the invention there is provided the use of Compound (I), or a pharmaceutically acceptable salt thereof, in the prevention of bone metastases in a warm blooded animal such as man.

In another aspect of the invention there is provided the use of Compound (I), or a pharmaceutically acceptable salt thereof, in the manufacture of a medicament for use in the prevention of bone metastases in a warm blooded animal such as man.

In another aspect of the invention there is provided a method of preventing bone metastases which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use in the prevention of bone metastases in a warm blooded animal such as man.

In another aspect of the invention there is provided the use of Compound (I), or a pharmaceutically acceptable salt thereof, in the treatment of bone metastases in a warm blooded animal such as man.

In another aspect of the invention there is provided the use of Compound (I), or a pharmaceutically acceptable salt thereof, in the manufacture of a medicament for use in the treatment of bone metastases in a warm blooded animal such as man.

In another aspect of the invention there is provided a method of treating bone metastases which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use in the treatment of bone metastases in a warm blooded animal such as man.

In a further aspect of the invention, there is provided the inhibition, treatment and/or prevention of bone metastases, as described herein, wherein the bone metastases are as a result of renal, thyroid, lung, breast or prostate cancer.

In another aspect of the invention there is provided the use of Compound (I), or a pharmaceutically acceptable salt thereof, in the prevention or treatment of pain associated with elevated endothelin-1 production in a warm blooded animal such as man.

In another aspect of the invention there is provided the use of Compound (I), or a pharmaceutically acceptable salt thereof, in the manufacture of a medicament for use in the prevention or treatment of pain associated with elevated endothelin-1 production in a warm blooded animal such as man.

In another aspect of the invention there is provided a method of treating pain associated with elevated endothelin-1 production which comprises administering an effective amount of Compound (I), or a pharmaceutically acceptable salt thereof, to a warm blooded animal such as man.

According to a further feature of this aspect of the invention there is provided a pharmaceutical composition which comprises Compound (I), or a pharmaceutically acceptable salt thereof, in association with a pharmaceutically acceptable diluent or carrier for use in the prevention or treatment of pain associated with elevated endothelin-1 production in a warm blooded animal such as man.

In another aspect of the invention there is provided the use of Compound (I), or a pharmaceutically acceptable salt thereof, in the prevention or treatment of pain in a warm blooded animal such as man.

In another aspect of the invention there is provided the use of Compound (I), or a pharmaceutically acceptable salt thereof, in the manufacture of a medicament for use in the prevention or treatment of pain in a warm blooded animal such as man.

In another aspect of the invention there is provided a method of treating pain which comprises administering an effective amount of Compound (I), or a pharmaceutically acceptable salt thereof, to a warm blooded animal such as man.

In another aspect of the invention there is provided the use of Compound (I), or a pharmaceutically acceptable salt thereof, in the prevention or treatment of pain associated with stimulation of the $ET_A$ receptor in a warm blooded animal such as man.

In another aspect of the invention there is provided the use of Compound (I), or a pharmaceutically acceptable salt thereof, in the manufacture of a medicament for use in the prevention or treatment of pain associated with stimulation of the $ET_A$ receptor in a warm blooded animal such as man.

In another aspect of the invention there is provided a method of treating pain associated with stimulation of the $ET_A$ receptor which comprises administering an effective amount of Compound (I), or a pharmaceutically acceptable salt thereof, to a warm blooded animal such as man.

Where cancer is referred to, particularly it refers to oesophageal cancer, myeloma, hepatocellular, pancreatic, cervical cancer, ewings tumour, neuroblastoma, Kaposis sarcoma, ovarian cancer, breast cancer, colorectal cancer, prostate cancer, bladder cancer, melanoma, lung cancer—non small cell lung cancer (NSCLC), and small cell lung cancer (SCLC)—gastric cancer, head and neck cancer, renal cancer, lymphoma and leukaemia. More particularly it refers to prostate cancer. In addition, more particularly it refers to SCLC, NSCLC, colorectal cancer, ovarian cancer and/or breast cancer. In addition, more particularly it refers to SCLC. In addition, more particularly it refers to NSCLC. In addition, more particularly it refers to colorectal cancer. In addition, more particularly it refers to ovarian cancer. In addition, more particularly it refers to breast cancer. Furthermore, more particularly it refers to bladder cancer, oesophageal cancer, gastric cancer, melanoma, cervical cancer and/or renal cancer. In addition it refers to endometrial, liver, stomach, thyroid, rectal and/or brain cancer. In another aspect of the invention, the cancer is not melanoma. In another embodiment of the invention, particularly the cancer is in a metastatic state, and more particularly the cancer produces metastases to the bone. In a further embodiment of the invention, particularly the cancer is in a metastatic state, and more particularly the cancer produces skin metastases. In a further embodiment of the invention, particularly the cancer is in a metastatic state, and more particularly the cancer produces lymphatic metastases. In a further embodiment of the invention, the cancer is in a non-metastatic state.

It is to be understood that when the cancer is in a metastatic state, that Compound (I) acts at both the primary tumour site and the metastases. Compound (I) both prevents, treats and inhibits metastases.

In one aspect of the invention, where pain is referred to, this is pain associated with raised endothelin-1 levels. In another aspect of the invention this is pain associated with stimulation of the $ET_A$ receptor resulting from situations where $ET_B$ down-regulation has occurred leading to abnormal $ET_A$ stimulation and/or elevation of endothelin-1 levels. Particularly this is pain associated with cancer. More particularly it is pain associated with prostate cancer.

According to a further feature of this aspect of the invention there is provided a pharmaceutical composition which comprises Compound (I), or a pharmaceutically acceptable salt thereof, in association with a pharmaceutically acceptable diluent or carrier for use in the prevention or treatment of pain associated with stimulation of the $ET_A$ receptor in a warm blooded animal such as man.

Additionally, Compound (I) is expected to be useful in the treatment and/or prophylaxis of pain of different origins and causes, including acute as well as chronic pain states. Examples are pain caused by chemical, mechanical, radiation (including sunburn), thermal (including burns), infectious or inflammatory tissue trauma or cancer, postoperative pain, postpartum pain, the pain associated with joint conditions (such as rheumatoid arthritis and osteoarthritis), pain associated with dental conditions (such as dental caries and gingivitis), myofascial and low back pain, pain associated with bone disorders (such as osteoporosis, hypercalcaemia of malignancy and Paget's disease) and the pain associated with sports injuries and sprains.

Also neuropathic pain conditions of central or peripheral origin could be treated or prevented with Compound (I). Examples of these pain conditions are pain associated with trigeminal neuralgia, pain associated with postherpetic neuralgia (PHN), pain associated with diabetic mono/poly neuropathy, pain associated with nerve trauma, pain associated with spinal cord injury, pain associated with central post stroke, pain associated with multiple sclerosis and pain associated with Parkinson's disease.

Other pain states of visceral origin such as caused by ulcer, dysmenorrhea, endometriosis, irritable bowel syndrome, dyspepsia, pelvic pain etc. could also be treated or prevented with Compound (I).

Additionally, Compound (I) is expected to be useful in the treatment and/or prophylaxis of additional types of pain for example complex regional pain syndrome, vasospastic/ischemic pains (e.g. Raynaud syndrome) and bone pain.

A further aspect of the invention is to use Compound (I) for oral treatment of neuropathic or central pain states.

Suitable pharmaceutically-acceptable salts include, for example, salts with alkali metal (such as sodium, potassium or lithium), alkaline earth metals (such as calcium or magnesium), ammonium salts, and salts with organic bases affording physiologically acceptable cations, such as salts with methylamine, dimethylamine, trimethylamine, piperidine and morpholine. In addition, suitable pharmaceutically-acceptable salts include, pharmaceutically-acceptable acid-addition salts with hydrogen halides, sulphuric acid, phosphoric acid and with organic acids such as citric acid, maleic acid, methanesulphonic acid and p-toluenesulphonic acid.

LEGENDS TO FIGURES

FIG. 1: This is a Western Blot showing inhibition of ET-1 induced MAPK phosphorylation with Compound (I) in the osteoblast cell line MC3T3.E1/J1 from study 2 below. The proteins have been run on a gel then transferred over to a nitrocellulose membrane, where they are probed for using the primary and secondary antibodies. The following abbreviations are used:

SCM: serum containing media

SFM: serum free media

Figure 2:
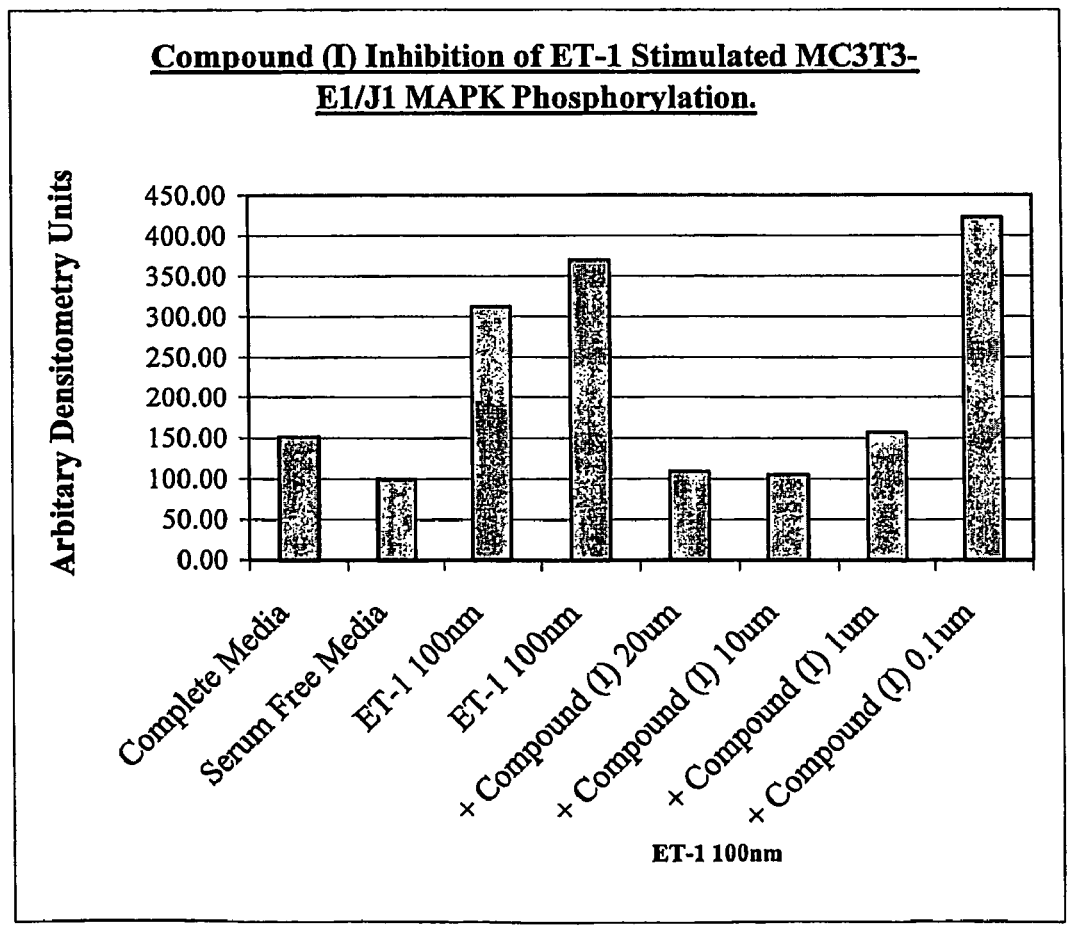

FIG. 2: This is a graph depicting, inhibition of ET-1 induced MAPK phosphorylation with Compound (I) in the osteoblast cell line MC3T3. E1/J1 also from study 2.

The following in vivo and in vitro studies can be used to determine the efficacy of Compound (I) in oncology.

1) Endothelin Human Receptor Binding Assay

Human recombinant $ET_A$ or $ET_B$ receptors were expressed in mouse erythroleukaemic (MEL) cells and membranes prepared for competition binding studies using $^{125}$I-labelled ET-1 as the radioligand. Incubations were carried out in triplicate in the presence of Compound (I), $10^{-10}$-$10^{-4}$ M in half log increments, and inhibition of ET-1 binding was expressed as a geometric mean $pIC_{50}$ value with 95% confidence limits.

Results

The $pIC_{50}$ (negative log of the concentration of compound required to displace 50% of the ligand) for Compound (I) at the $ET_A$ receptor was 8.27 [8.23-8.32] (n=4). Displacement curves were normal with slopes close to unity. Compound (I) had no measurable affinity for the $ET_B$ receptor with a mean displacement of 1.2±0.7% (n=3) at a concentration of $10^{-4}$M, a figure well within the limits of sensitivity of the assay.

Conclusion

Compound (I) is a high affinity ligand for the human $ET_A$ receptor and is $ET_A$ specific, having no significant $ET_B$ receptor affinity.

2) Compound (I) as a Treatment for Metastatic Cancer: Osteoblast Data—Inhibition of ET-1 Induced MAPK Stimulation with Compound (I)

Compound (I) may well have a role in the treatment of not only primary tumours but also metastatic tumours and the pathological production of new bone in and around metastatic deposits. Described below is an experiment demonstrating the utility of Compound (I) in treating the osteoblastic bone pathology.

The important clinical pathology seen in the bone metastatic regions of patients with advanced prostate cancer presents as an inappropriate osteoblastic stimulation, i.e. the presence of prostatic tumour metastases in bone results in the net production of new bone and eventually an increase in bone density around the metastatic deposit (reviewed in Cancer Metastasis Rev. 2001; 20(34):33349). The hypothesised mechanism behind this pathology is a release of ET-1 from the metastatic prostate cell in the early establishment of the secondary bone tumour.

ET-1 stimulation of the osteoblast has been described as the key step in the pathological formation of new bone in prostate bone metastasis (Invest New Drugs. 2002; 20(2):173-82). It has been shown that ET-1 acts to directly induce proliferation and differentiation of the osteoblast, as well as stimulate the osteoblast to produce other growth factors, by simulation of the $ET_A$ receptor and subsequent phosphorylation of MAP kinase (Bone. 1999; 24(4):315-20 and J Bone Miner Res. 2002; 17(10):1774-84). In this way stimulation of the $ET_A$ receptor causes both growth of bone and also, by release of growth factors into the local environment, survival and growth of the metastatic tumour cell. The tumour cells and osteoblastic cells in a metastatic deposit therefore participate in a "vicious cycle" in which their proliferative responses support each other, overcoming the normal regulatory mechanisms which control and limit bone formation (Nat Rev Cancer. 2002; 2(8): 584-93).

In the experiments described below the present inventors first demonstrate the ability of ET-1 to stimulate MAP kinase in osteoblastic cells. This stimulation promotes proliferation of the cells and activation of the pathways shown to be important in the release of growth factors from the osteoblast.

The inventors then demonstrate that Compound (I), an $ET_A$ antagonist is an effective antagonist of this ET-1 stimulation.

Method

The MC3T3. E1/J1 cell line was isolated from a parental cell line, MC3T3-E1 (available from Invitrogen), which had in turn been derived from newborn C57BL/6 mouse calvaria. The MC3T3 E1/J1 line is described as an osteoblastic line. To initiate the experiments described below, MC3T3.E1/J1 cells were plated at a density of $2.4 \times 10^4$ cells/well (24 well plates) in serum containing media and incubated for 48 hours. The cells were washed twice in PBS and re-incubated for approximately 17 hours in serum starvation media.

At this stage, cells were then incubated with or without Compound (I) for 30 minutes then stimulated with growth factor (PDGF or ET-1) for 3 minutes. All media was then removed and the cells lysed and stored at −20° C. for electrophoresis/western blot, which localized phosphorylated MAPK and phosphorylated Akt probing with anti-phospho-p44/42 MAPK (Thr 202/204) and anti-Phospho AKT (Ser 473) antibodies (both commercially available from Cell Signalling Technology). The protein bands were quantitated by densitometry, and plotted as arbitrary densitometry units. Phosphorylated MAPK levels were normalised to total MAPK levels.

Results

Stimulation of cells with ET-1 for 3 minutes resulted in increased phosphorylation of MAPK in the osteoblast cell line MC3T3.E1/J1. Stimulation of the cells with a standard growth factor, PDGF, also resulted in increased phosphorylation of MAPK. Compound (I) inhibited ET-1-induced MAPK phosphorylation in osteoblasts.

TABLE 1

Inhibition of ET-1 induced MAPK phosphorylation with Compound (I) in the osteoblast cell line MC3T3.E1/J1

| Environment | Average |
| --- | --- |
| Complete Media | 151.70 |
| Serum Free Media | 100.00 |
| ET-1 100 nm | 312.78 |
| ET-1 100 nm | 369.85 |
| +Compound (I) 20 µm | 109.18 |
| +Compound (I) 10 µm | 105.15 |
| +Compound (I) 1 µm | 157.41 |
| +Compound (I) 0.1 µm | 422.11 |

This data is represented in FIGS. 1 and 2.

Note: The above experiment is not reliant on use of the particular MC3T3.E1/J1 cell line, it could, for example, be performed using the commercially available parental cell line MC3T3-E1.

3) Compound (I) as an Inhibitor of Angiogenesis $ET_A$ receptor activation by ET-1 contributes to tumour growth and progression, mediated by various mechanisms in the literature to suggest that specifically inhibiting $ET_A$ will produce beneficial effects on primary tumours quite separate to its effects on bone metastases. These mechanisms include anti-apoptosis, direct and indirect growth promotion and promotion of cell motility (Nat Rev Cancer. 2003; 3(2): 110-6).

Of more recent and increasing interest is the role of ET-1 mediated by the $ET_A$ receptor as key players in tumour angiogenesis (J Cardiovasc Pharmacol. 2000; 36: S135-9). Mechanistic studies have now shown that the $ET_A$ receptor is important in the production of the potent angiogenic factor VEGF (Life Sci. 1998; 63(6): 477-84) by direct induction of a hypoxia-inducible factor, HIF-1α (J Biol Chem. 2002; 277: 27850-5). The increasing literature to support the role of endothelin and the $ET_A$ receptor in tumour angiogenesis was reviewed very recently by Bagnato and Spinella, (Trends Endocrinol Metab. 2003; 14(1): 44-50).

In the experiment described below we show the effect of Compound (I) on the angiogenesis induced by newly formed tumours following human tumour cell inoculation in animal models.

Method

Tumour cells were inoculated intra-dermally in nude mice, Compound (I) 25 or 50 mg/kg or vehicle was given once daily p.o. with the first dose given on the day after cell implantation and the mice were sacrificed 5 days later. A 1 cm² area with the tumour at the centre was examined and the number of blood vessels bifurcations within that area supplying the tumour were counted. The number of vessels supplying tumours from animals treated with test drug and vehicle were compared and the effect of Compound (I) was calculated as a percentage reduction of vessel count.

Results

Compound (I) caused reductions in blood vessel density around tumours in treated animals compared to vehicle controls. Reductions in vessel counts by Compound (I) were seen around tumours induced by both colon and prostate cell lines in five in vivo studies.

TABLE 2

Inhibition of angiogenesis in primary tumours caused by Compound (I)

| Cell Line | Tumour Type | Compound (I) dose (mg/kg) | Inhibition of vessel count [1] |
|---|---|---|---|
| LOVO | Colon | 50 | 20% (P = 0.001) |
| LOVO | Colon | 50 | 28% (P < 0.001) |
| LOVO | Colon | 25 | 28% (P < 0.001) |
| DU145 | Prostate | 50 | 30% (P < 0.05) |
| DU145 | Prostate | 25 | 38% (P < 0.001) |

[1] statistically analyzed by the ANOVA test compared to vehicle controls
The above cells lines are commercially available. One source is the ATCC (American Type Culture Collection). LOVO has ATCC No = CCL-229. DU145 has ATCC No = HTB-81.

Discussion

We have shown that, in vitro, Compound (I) is an effective inhibitor of ET-1 mediated activation of MAP kinase in osteoblasts as well as being effective in inhibiting angiogenesis in primary tumours in vivo. This confirms the potential for this agent as a therapy in metastatic prostate cancer as it may have beneficial effects in preventing pathological bone density increases (by inhibition of osteoblastic proliferation), mediated by MAPK pathway as well as inhibiting the release of growth factors which support the survival and growth of tumour cells in the bone microenvironment in addition to anti-angiogenesis effect at the primary tumour.

4) Compound (I) as an Endothelin Receptor Antagonist in the Human Endothelin System Human forearm blood flow can be assessed by temporarily impeding the venous drainage from the arm by the application of a pneumatic cuff on the upper arm, which is then inflated to just above venous pressure. The resulting arterial flow into the arm with no corresponding venous drainage leads to engorgement and swelling of the forearm, which can be detected with sensitive strain gauges. Infusion of the arterial vasoconstrictor ET-1 into the brachial artery leads to a reduction in forearm distension due to decreased arterial inflow. This vasoconstriction is mediated via endothelin receptors on the vascular endothelium and associated smooth muscle.

Method

A study was performed to investigate the ability of Compound (I) to antagonise the vasoconstrictor effect of ET-1 via endothelin receptors in this model in healthy male subjects aged 18-65. Eight subjects received single oral doses of 10 mg Compound (I), 30 mg Compound (I) and placebo in a randomised, double blind manner on study days at least 7 days apart. Forearm vasoconstriction in response to ET1 was assessed between 2 and 4 hours post dosing with Compound (I).

Results

Overall, Compound (I) produced a statistically significant reduction in forearm blood flow in response to infused ET-1 compared to placebo (p=0.0210) with evidence of a dose response between the doses investigated. This demonstrates that Compound (I) is an endothelin receptor antagonist in the human endothelin system.

5) Compound (I) in a Dose-Escalation Study to Assess the Tolerability and Pharmacokinetics of Compound (I) given Orally Once Daily in Patient With Metastatic Prostate Cancer The following study can be undertaken to determine the maximum well tolerated dose (MWTD) of Compound (I) in subjects with metastatic prostate cancer. This study will allow you to observe the effect of Compound (I) on prostate-specific antigen (PSA), observe the effect of Compound (I) on a serological biomarker of bone metastasis and provide you with pharmacokinetic characterization of Compound (I) in subjects with metastatic prostate cancer.

Method

Patients with prostate cancer who have documented bone metastases (confirmed by bone scan within 3 months of study entry) can be used for this study. Compound (I) can be given orally once daily in tablet form. 120 mg can be used as the starting dose. Subjects can be given study medication for 28 days or until withdrawal criteria are met. Each dose level can recruit up to three subjects with metastatic prostate cancer.

A formal assessment of tolerability can be made in each subject following one week of Compound (I) administration. Dose escalation can occur when two subjects in any cohort have not experienced a dose limiting toxicity (DLT) following one week of continuous Compound (I) administration. The dose can escalate by a factor of two at each step. If one subject at a particular dose level has a DLT, then two additional subjects at the same dose level must not experience DLTs in order to escalate to the next dose level.

Subjects can continue therapy for twenty eight days unless the withdrawal criteria are met. When a minimum of two subjects in any cohort have been given a dose that is considered to be not well tolerated at any time point after administration, dose escalation will end, and the closest dose below this will be taken as the MWTD.

The following outcomes can be observed:
Incidence and severity of adverse events;
PSA concentration (total and ratio of free to total) at 1, 2, and 4 weeks in subjects treated with Compound (I);
Change in PSA (total and ratio of free to total) from before Compound (I) administration to 1, 2 and 4 weeks after Compound (I) administration;
Change in a serum marker of bony metastatic involvement (bone alkaline phosphatase) from the level before Compound (I) administration to levels after 1, 2, and 4 weeks of Compound (I) administration; and Plasma concentrations and variables of Compound (I) following a single dose and multiple doses at steady state.

Testing for Pain Relief

The analgesic effect of Compound (I) may be measured, for example, in the murine model of cancer pain described by Wacnik et al., Journal of Neuroscience (2001), 21, 9355.

In a further embodiment of the present invention Compound (I), or a pharmaceutically acceptable salt thereof, is administered to a cell or individual prior to the development of cancer. For example, a person at risk of developing cancer may be treated with Compound (I), or a pharmaceutically acceptable salt thereof, to prevent or inhibit the development of cancer and/or to prevent the development of metastases.

Compound (I), or a pharmaceutically acceptable salt thereof, can be administered for therapeutic or prophylactic use to a warm blooded animal such as man by methods known in the art. Administration can occur directly at the tumour site, or particularly, systemic administration.

Compound (I), or a pharmaceutically acceptable salt thereof, can be administered for therapeutic or prophylactic use to a warm blooded animal such as man in the form of conventional pharmaceutical compositions. The composition may be in a form suitable for oral administration, for example as a tablet or capsule, for parenteral injection (including intravenous, subcutaneous, intramuscular, intravascular or infusion) as a sterile solution, suspension or emulsion, for topical administration as an ointment or cream or for rectal administration as a suppository. In general the above compositions may be prepared in a conventional manner using conventional excipients. For example, Compound (I) can be formulated as a tablet using the following excipients:

Compound (I);
Lactose monohydrate (filler);
Croscarmellose sodium (disintegrant);
Povidone (binder);
Magnesium stearate (lubricant);
Hypromellose (film coat component);
Polyethylene glycol 300 (film coat component); and
Titanium dioxide (film coat component).

The amount of Compound (I), or a pharmaceutically acceptable salt thereof, administered would be that sufficient to provide the desired pharmaceutical effect. For instance, Compound (I) could be administered to a warm-blooded animal orally, at a unit dose less than 1 g daily. Particularly Compound (I) could be administered to a warm-blooded animal, at a unit dose of less than 250 mg per day. In another aspect of the invention, Compound (I) could be administered to a warm-blooded animal, at a unit dose of less than 130 mg per day. In a further aspect of the invention, Compound (I) could be administered to a warm-blooded animal, at a unit dose of less than 50 mg per day.

The invention claimed is:

1. A method of treating prostate cancer which comprises administering an effective amount for treating prostate cancer of N-(3-methoxy-5-methylpyrazin-2-yl)-2-(4-[1,3,4-oxadiazol-2-yl]phenyl)pyridine-3-sulphonamide, or a pharmaceutically acceptable salt thereof, to a warm blooded animal in need of treatment of prostate cancer.

2. The method according to claim 1 wherein the prostate cancer is in a metastatic state.

3. The method according to claim 1 wherein the prostate cancer is in a non-metastatic state.

4. The method according to claim 1 wherein the prostate cancer is producing bone metastases.

5. The method according to claim 1 wherein the warm blooded animal is man.

6. A method for reducing abnormal proliferation in a prostate cancer cell or inducing differentiation of a prostate cancer cell which comprises administering an effective amount for reducing abnormal proliferation in a prostate cancer cell or inducing differentiation of a prostate cancer cell of N-(3-methoxy-5-methylpyrazin-2-yl)-2-(4-[1,3,4-oxadiazol-2-yl]phenyl)pyridine-3-sulphonamide, or a pharmaceutically acceptable salt thereof, to a warm blooded animal in need of reduction of abnormal proliferation of a prostate cancer cell or in need of inducing differentiation of a prostate cancer cell.

7. The method according to claim 6 wherein the warm blooded animal is man.

8. A method of inducing apoptosis in a prostate cancer cell which comprises administering an effective amount for inducing apoptosis in a prostate cancer cell of N-(3-methoxy-5-methylpyrazin-2-yl)-2-(4-[1,3,4-oxadiazol-2-yl]phenyl)pyridine-3-sulphonamide, or a pharmaceutically acceptable salt thereof, to a warm blooded animal in need of inducing apoptosis in a prostate cancer cell.

9. The method according to claim 8 wherein the warm blooded animal is man.

* * * * *